United States Patent [19]

Bailey et al.

[11] Patent Number: 4,800,167

[45] Date of Patent: Jan. 24, 1989

[54] REAGENT AND PROCESS FOR THE DETERMINATION OF HEMOGLOBIN IN BLOOD

[75] Inventors: Mark W. Bailey, Highland Park; Myrna G. Ulanday, Libertyville, both of Ill.

[73] Assignee: Abbott Laboratories, North Chicago, Ill.

[21] Appl. No.: 36,604

[22] Filed: Apr. 10, 1987

[51] Int. Cl.$^4$ ............................................. G01N 33/72
[52] U.S. Cl. ............................................................. 436/66
[58] Field of Search ............... 436/66, 67, 68; 356/40, 356/36

[56] References Cited

U.S. PATENT DOCUMENTS 4,341,527  7/1982  Zander et al. .................... 436/66
4,673,654  6/1987  Talmage ............................ 422/57

FOREIGN PATENT DOCUMENTS

220143 A-1  3/1985  German Democratic Rep. .

OTHER PUBLICATIONS

Lyonnais et al., J. Lab. Clin. Med., (85)2, pp. 329–336 (1975).

*Primary Examiner*—Michael S. Marcus
*Assistant Examiner*—Lyle Alfandary-Alexander
*Attorney, Agent, or Firm*—Thomas D. Brainard; Donald L. Corneglio; Martin L. Katz

[57] ABSTRACT

A reagent system for determing the hemoglobin content of whole blood comprising an aqueous solution of polyvinylpyrrolidone of molecular weight from about 10,000 to about 360,000 at a pH greater than about 8.0 to denature hemoglobin in whole blood. A method is also provided wherein a blood sample is treted with an aqueous solution of polyvinylpyrrolidone of molecular weight from about 10,000 to about 360,000 at a basic pH sufficient to denature the hemoglobin present in the whole blood to form a stable product whereafter the absorbance of the stable product of the blood sample and polyvinylpyrrolidone of molecular weight from about 10,000 to about 360,000 polymer reagent system is measured at a wavelength of approximately 575 nm to determine the hemoglobin contentration.

9 Claims, No Drawings

REAGENT AND PROCESS FOR THE DETERMINATION OF HEMOGLOBIN IN BLOOD

BACKGROUND OF THE INVENTION

The present invention is directed towards a new reagent system for determining the hemoglobin content of whole blood. The quantitative determination of hemoglobin in whole blood is one of the most frequently performed analyses in clinical chemistry. It is, therefore, desirable to develop new, safe and reliable methods for performing this analysis.

The most frequently performed spectrophotometric analysis uses a method known as the cyanomethemoglobin method which has been universally accepted and is now used worldwide. A serious drawback to the cyanomethemoglobin method is that the reagent is a highly toxic chemical and, therefore, extreme care must be used when handling this reagent.

An alternative method to the cyanomethemoglobin method is disclosed in U.S. Pat. No. 4,341,527. The patent discloses a water-soluble liquid nitrogen-free non-ionic detergent such as polyethyleneglycol p-alkylphenyl ether and various derivatives thereof. This approach uses a non toxic surfactant to stabilize the heme and hemoglobin derivatives of the denatured blood such that a photometric determination of the hemoglobin content of the blood sample can be performed. An unfortunate drawback to this method, however, is that because a surfactant is employed, the surface tension of the aqueous reagent solution is reduced, which presents problems in handling the reagent. In particular, the lower surface tension of the reagent presents problems in transferring the reagent by pipette. The low surface tension also presents problems in packaging the reagent because of the tendency to adhere to packaging surfaces. It is, therefore, desirable to develop a new reagent system for the determination of the hemoglobin content of whole blood which has the advantage of being non-toxic without reducing the surface tension which presents problems in processing and handling of the reagent.

SUMMARY OF THE INVENTION

The present invention provides for a reagent for determining the hemoglobin content of whole blood which employs an aqueous solution of a polymer. The subject reagent does not reduce the surface tension of the aqueous solution and is easily packaged and handled. Further, the reagent is non-toxic.

In one aspect, the present invention is directed toward a reagent for determining the hemoglobin content of whole blood comprising an aqueous solution of polyvinyloxynolidone at a pH sufficient to denature the hemoglobin. Upon addition of the reagent to a blood sample, all the heme and hemoglobin derivatives occurring in blood are solubilized to form a stable product having a photometric absorbance maximum at a wavelength of about 575 nanometers (nm). The reagent system of the subject invention preferably employs an aqueous solution at a pH of about 12 or higher, which is sufficient to denature the hemoglobin.

In another aspect the present invention is directed toward a method for determining the hemoglobin content of whole blood. The method comprises adding an aqueous solution of polyvinylpyrrolidone at a pH sufficient to denature the hemoglobin whereby the hemoglobin is solubilized to form a stable product having a photometric absorbance, at a wavelength of about 575 nm. The preferred pH for performing the method is over a pH range from about 12 to 14. A distinct advantage of the present invention is that it employs a reagent system in the absence of a surfactant whereby the reagent can be easily handled and packaged for subsequent use as a reagent for determining the hemoglobin content of whole blood. The particular reagent system is a stable and non-toxic reagent having reduced sensitivity to interfering substances, i.e. lipemia and bilirubin. The present reagent has been compared to traditional hemoglobin reagent systems with excellent correlation.

DETAILED DESCRIPTION OF THE INVENTION

The present invention provides for a reagent system for determining the hemoglobin content of whole blood. The reagent system comprises an aqueous solution of a polyvinylpyrrolidone (PVP). PVP is a nitrogen-based water soluble polymer which in the presence of denatured hemoglobin functions to stabilize the heme and hemoglobin derivatives of the blood such that an absorbance reading can be made at a wavelength of about 575 nm. The absorbance reading of a blood sample is directly proportional to the concentration of hemoglobin in the sample. The PVP reagent is especially advantageous in the performance of a hemoglobin determination because it is both a non-toxic reagent and does not reduce the surface tension of the solution as would a reagent system based upon a surfactant to stabilize the heme or hemoglobin derivatives of the blood.

The PVP polymer can be represented by the structural formula:

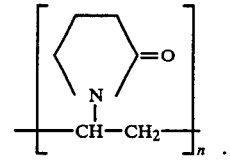

PVP polymer is available in a wide range of molecular weights which do not critically influence the performance of the reagent system. For example, molecular weights from about 10,000 to about 360,000 can be employed. The higher molecular weight PVP polymers tend to produce higher absorbance for equivalent amounts of hemoglobin. However, the higher absorbance does not effect the accuracy of the hemoglobin determination because the absorbance signals are calibrated against hemoglobin standards.

The PVP polymer is dissolved in an aqueous solution having a pH sufficiently high to denature hemoglobin in a blood sample. A pH sufficient to denature hemoglobin in a blood sample in a timely and efficient manner is generally considered to be at about 12 to about 14. Therefore, a quantity of PVP is dissolved in an aqueous solution which has been treated with a base in order to elevate the pH to a desired range of more than 8, more preferably, from about 12 to about 14. The PVP is added to the aqueous solution in an amount from about 0.01 to about 10.0, more perferably, from about 0.75 to about 1.25 percent weight/volume.

Any of a number of bases can be employed to elevate the pH of the aqueous solution to the desired range. All that is critical is that the pH of the aqueous solution be sufficiently hiqh such that when it is added to the blood sample, the hemoglobin in the blood is denatured. Particularly preferred are salts of hydroxide such as sodium hydroxide, potassium hydroxide or lithium hydroxide. It has generally been found that a salt of hydroxide can be added to the aqueous solution to form a 0.1 molar solution which is sufficiently high pH to denature blood.

For example, the reagent of the subject invention can be prepared by adding ten grams of a dry powder of PVP and 4.2 grams of lithium hydroxide to 500 ml. of sterile distilled water in a one-liter volumetric flask. The contents of the flask are mixed until all the dry components have completely dissolved. After the components have dissolved, the flask is then filled to the one-liter mark. The reagent is stable and may be stored at room temperature.

The test procedure for performing the method of determining the hemoglobin content of whole blood is generally performed by reading the absorbance of a blood sample mixed with the a basic, aqueous, solution of PVP at a wavelength of about 575 nm. About five to 10 ml of the basic aqueous reagent is mixed with 100 microliters of whole blood. After the blood sample is treated with the reagent system, the absorbance of the reaction product is read at a wavelength of about 575 nm using water as a blank. The absorbance reading of the sample is directly proportional to the concentration of hemoglobin in the sample. Typically, a three-point standard curve is employed to calculate the sample hemoglobin concentration using the formula as follows:

$$Hb \text{ concentration} = \frac{Abs_{575} - y \text{ intercept}}{\text{slope}}$$

The test is compatible with any of a number of types of whole blood controls and calibrators.

The following examples are provided to illustrate the subject invention:

EXAMPLE 1

To a test tube containing 100 microliters of well-mixed whole blood specimen is added by pipette 7.5 ml of reagent. The reagent consisted of a one percent solution of PVP and 0.1 molar lithium hydroxide aqueous solution. The reagent was added to the whole blood specimen and well mixed for approximately five seconds. After mixing, the sample was allowed to stabilize for a period of about two minutes. After the sample had stabilized, the absorbance of the sample was read at a wavelength of 575 nm. A test tube containing a blank of water was also read at 575 nm for comparison to the sample.

The above procedure was performed on 18 separate samples containing varying amounts of hemoglobin. In addition to performing the subject method, each sample was also tested using a surfactant reagent system for comparison and correlation of data. The surfactant reagent system and method performed was similar to that as described in U.S. Pat. No. 4,341,527. The particular surfactant employed was Igepal ® surfactant commercially available from the GAF Corporation, Wayne, New Jersey. The surfactant is a clear viscous liquid. Igepal ® was employed in the amount of 2.5% w/v in a 0.1 molar aqueous solution of lithium hydroxide. Each of the 18 blood specimen samples were run in an identical fashion and the absorbance of the reaction product measured at 595 nm. The results of the absorbence measurements are shown below in Table 1. The whole blood specimen concentration of hemoglobin ranged from approximately 6 to 18 grams per deciliter.

TABLE I

| Blood Specimen | Reagent System (g/dL) Igepal ® | PVP Polymer | Blood Specimen | Reagent System (g/dL) Igepal ® | PVP Polymer |
|---|---|---|---|---|---|
| 1 | 6.1 | 6.2 | 10 | 11.0 | 10.7 |
| 2 | 16.3 | 16.0 | 11 | 13.5 | 13.4 |
| 3 | 17.4 | 16.8 | 12 | 18.6 | 17.7 |
| 4 | 9.0 | 9.0 | 13 | 10.1 | 9.8 |
| 5 | 14.9 | 14.9 | 14 | 13.3 | 13.1 |
| 6 | 11.1 | 10.9 | 15 | 13.8 | 13.5 |
| 7 | 12.5 | 12.3 | 16 | 11.9 | 11.7 |
| 8 | 16.4 | 15.8 | 17 | 17.1 | 16.2 |
| 9 | 12.8 | 12.7 | 18 | 12.3 | 11.9 |

The table shows an excellent correlation between the surfactant reagent form of a hemoglobin test method and the instant invention which employs a polymer of polyvinylpyrrolidone (PVP). A significant advantage, however, of the subject invention, is that the reagent system did not have a reduced surface tension which greatly enhanced the ability to handle and pipette the reagent.

The use of a polymer to stabilize the heme and hemoglobin derivatives in whole blood also has the unexpected characteristics of not being subject to significant lipemic interference from hemoglobin Commonly, lipid turbidity is present in serum and blood samples used in clinical assays due to elevated lipid concentrations in blood. The lipemia causes turbidity in samples which interferes with spectrophotomeric measurements by causing light scattering and optical aberration. Attempts to remedy this problem have included the addition of surfactants to the reagent system such as Igepal ®, which is a trademark for polyethyleneglycol alkylphenyl ether commercially available from the GAF corporation, Wayne, New Jersey. It was therefore expected that substituting a water soluble polymer and eliminating the surfactant from the reagent system would present problems with lipemic interference for hemoglobin determination.

Interestingly, the use of PVP polymer as a reagent system in the determination of hemoglobin has not presented lipemic interference problems which would be expected in the absence of a surfactant reagent system. Therefore, the use of a PVP polymer reagent system does not present lipemic interference problems which would normally be associated with a non-surfactant containing reagent system. This is exemplified in Example 2 where various blood specimens were run with a Igepal ® containing reagent system and a PVP containing reagent system and lipemic interference was measured for each sample tested.

EXAMPLE 2

Eight blood specimen samples (A-H) having various amounts of plasma lipid (triglyceride in mg/dl) were tested using the two procedures described in Example 1. Interference greater than approximately ten percent is considered to be unacceptable for performing clinical chemistry assays of hemoglobin content. While all the samples tested using both procedures performed well beneath the ten percent limit, it was interesting to see that the PVP polymer reagent system performed very well, i.e. interference less than ten percent, and in some cases, performed even better than the surfactant reagent system. The results of the eight specimens tested are shown below in Table II.

TABLE II

| Blood Specimen (triglyceride content mg/dl) | % Lipemic Interference | |
|---|---|---|
| | Igepal ® | PVP Polymer |
| A 559 | 2.00 | 1.75 |
| B 575 | −.25 | −2.50 |
| C 713 | −1.00 | 1.00 |
| D 801 | 3.00 | 3.00 |
| E 899 | 1.25 | 2.00 |
| F 1237 | 3.00 | 1.00 |
| G 1533 | 5.00 | 8.25 |
| H 4562 | .50 | 7.75 |

The data shown in Table II indicates that the PVP polymer reagent system and method was successful in performing hemoglobin determinations of whole blood samples with minimal lipemic interference.

We claim:

1. A reagent for determining the hemoglobin content of whole blood comprising:
   an aqueous solution of polyvinylpyrrolidone of molecular weight from about 10,000 to about 360,000 at a pH greater than about 8.0 to denature hemoglobin in whole blood whereby, upon addition to a blood sample, all hemoglobin derivatives are solubilized to form a product having a maximum photometric absorbance at a wavelength of about 575 nm.

2. The reagent of claim 1 wherein said aqueous solution is at a pH of about 12 to about 14.

3. The reagent of claim 1 wherein said polyvinylpyrrolidone is present in an amount of from about 0.01 to 10.0% weight/volume of solution.

4. The reagent of claim 1 which includes a hydroxide salt to adjust the pH.

5. The reagent of claim 4 wherein said hydroxide salt is NaOH, KOH or LiOH.

6. A method for determining the hemoglobin content of whole blood comprising:
   treating blood with an aqueous solution of polyvinylpyrrolidone to denature hemoglobin in the blood, and measuring the absorption of the treated blood at about 575 nm.

7. The method of claim 6 wherein said pH is about 12 to about 14.

8. The method of claim 6 wherein the concentration of said polyvinylpyrrolidone in said aqueous solution is from about 0.01% to about 10.0% weight/volume of solution.

9. The method of claim 6 wherein about 100 microliters of whole blood is treated with about 5.0 to about 10 ml of said aqueous solution.

* * * * *

UNITED STATES PATENT AND TRADEMARK OFFICE
CERTIFICATE OF CORRECTION

PATENT NO. : 4,800,167
DATED : January 24, 1989
INVENTOR(S) : Mark W. Bailey, et al.

It is certified that error appears in the above—identified patent and that said Letters Patent is hereby corrected as shown below:

In the Abstract, line 6, change "treted" to --treated--.

In Claim 6, line 4, after "polyvinylpyrrolidone" insert --of molecular weight from about 10,000 to about 360,000 at a pH greater than about 8.0--.

Signed and Sealed this

Fourth Day of July, 1989

Attest:

DONALD J. QUIGG

Attesting Officer

Commissioner of Patents and Trademarks